(12) United States Patent
Niu et al.

(10) Patent No.: US 11,028,377 B2
(45) Date of Patent: Jun. 8, 2021

(54) PHYTASE VARIANTS YKAPPA HAVING IMPROVED PEPSIN RESISTANCE AND INCREASED CATALYTIC EFFICIENCY

(71) Applicant: FEED RESEARCH INSTITUTE, CHINESE ACADEMY OF AGRICULTURAL SCIENCES, Beijing (CN)

(72) Inventors: Canfang Niu, Beijing (CN); Peilong Yang, Beijing (CN); Bin Yao, Beijing (CN); Yangyang Li, Beijing (CN); Dali Yu, Beijing (CN); Huiying Luo, Beijing (CN); Huoqing Huang, Beijing (CN); Yaru Wang, Beijing (CN)

(73) Assignee: FEED RESEARCH INSTITUTE CHINESE ACADEMY OF AGRICUT, Beijing (CN)

( * ) Notice: Subject to any disclaimer, the term of this patent is extended or adjusted under 35 U.S.C. 154(b) by 0 days.

(21) Appl. No.: 16/477,907

(22) PCT Filed: Jan. 15, 2018

(86) PCT No.: PCT/CN2018/072549
§ 371 (c)(1),
(2) Date: Jul. 15, 2019

(87) PCT Pub. No.: WO2018/130212
PCT Pub. Date: Jul. 19, 2018

(65) Prior Publication Data
US 2020/0277583 A1    Sep. 3, 2020

(30) Foreign Application Priority Data

Jan. 15, 2017  (CN) .......................... 201710027075.2

(51) Int. Cl.
*C12N 9/16* (2006.01)
*C07K 14/24* (2006.01)

(52) U.S. Cl.
CPC .............. *C12N 9/16* (2013.01); *C07K 14/24* (2013.01); *C12Y 301/03* (2013.01)

(58) Field of Classification Search
None
See application file for complete search history.

(56) References Cited

U.S. PATENT DOCUMENTS 9,765,313 B2 *  9/2017  Yao ........................ C12N 1/14

* cited by examiner

*Primary Examiner* — Anand U Desai
(74) *Attorney, Agent, or Firm* — Patshegen IP LLC; Moshe Pinchas

(57) ABSTRACT

The present invention relates to the field of genetic engineering, particularly to phytase variants YkAPPA having amino acid sequence substituting Leucine at the 162$^{th}$ site of the sequence set forth in SEQ ID NO.1 with glycine or proline, or having amino acid sequence substituting glutamic acid at the 230$^{th}$ site of the sequence set forth in SEQ ID NO.1 with glycine, alanine, serine, threonine, aspartic acid, proline, or arginine, and having improved pepsin resistance and increased catalytic efficiency of 2.1 times of that of the wild phytase, in the benefit of the development of economical feed enzyme industry.

6 Claims, 2 Drawing Sheets

Specification includes a Sequence Listing.

PHYTASE VARIANTS YKAPPA HAVING IMPROVED PEPSIN RESISTANCE AND INCREASED CATALYTIC EFFICIENCY

FIELD OF THE INVENTION

The present invention relates to the field of genetic engineering, particularly to phytase variants YkAPPA having improved pepsin resistance and increased catalytic efficiency.

BACKGROUND OF THE INVENTION

Phytase is an important industrial enzyme that can hydrolyze phytic acid into phosphoric acid residues. At present, the poor protease resistance of most phytase brings huge waste of phosphorus, increasing feed cost and polluting the environment. The phytase with protease resistance and high catalytic efficiency would reduce animal production costs, and produce good economic and ecological benefits.

With the development of protein structure and molecular biology, the artificial modification of enzyme molecule by directed evolution and rational design has become a research hotspot in the field of enzyme engineering

ORDER OF THE INVENTION

One order of the present invention is to provide phytase variants having improved pepsin resistance and increased catalytic efficiency by a method of site-directed mutagenesis.

Another order of the present invention is to provide a gene encoding the above phytase variants having improved pepsin resistance and increased catalytic efficiency.

Another order of the present invention is to provide a recombinant vector comprising the above gene encoding the above phytase variants having improved pepsin resistance and increased catalytic efficiency.

Another order of the present invention is to provide a recombinant cell comprising the above gene encoding the above phytase variants having improved pepsin resistance and increased catalytic efficiency.

SUMMARY OF THE INVENTION

One aspect of the present invention is to provide a site-directed mutation variants of phytase of which the mature protein has amino acid sequence as set forth in SEQ ID NO.1, encoded by SEQ ID NO.2.

```
                                        SEQ ID NO. 1
MTIAKEYLRLSILTLVLSSFTLSAAPLAAQSTGYTLERVVILSRHGVRSP

TKQTQLMNDVTPDKWPQWPVKAGYLTPRGAGLVTLMGGFYGDYFRSYGLL

PAGCPADESIYVQADVDQRTRLTGQAFLDGIAPDCGLKVHYQADLKKIDP

LFHTVEAGVCKLDPEKTHQAVEKRLGGPLNELSQRYAKPFALMGEVLNFS

ASPYCNSLQQKGKTCDFATFAANEIEVNKEGTKVSLSGPLALSSTLGEIF

LLQNSQAMPDVAWNRLSGEENWISLLSLHNAQFDLMAKTPYIARHKGTPL

LQQIDTALVLQRDAQGQTLPLSPQTKLLFLGGHDTNIANIAGMLGANWQL

PQQPDNTPPGGGLVFELWQNPDNHQRYVAVKMFYQTMEQLRNADKLDLKN

NPARIVPIAIEGCENEGDNKLCQLETFQKKVAQVIEPACHI.
```

```
                                        SEQ ID NO. 2
Atgacaatagcaaaagaatatctgcggttatccatactcactttggtgct cagtagttttacgctaagtgctgcaccgcttgcagcacaatctaccggtt acactttggagcgcgtggtgattttgagccgccacggtgttcgttcccccg acgaaacaaacacagttaatgaatgatgttacaccggacaaatggccaca atggccagtaaaagcgggctatttaacgccgcgagggcaggattagtca ctttaatgggcgggttctatggtgattatttccgcagctatgggttgtta ccggcggggtgcccggcagacgaatccatctatgtgcaagctgatgttga ccaacgtacccgcttaaccgggcaggcatttctggacggtatagccccgg attgcggcctgaaagtacattatcaagctgatttgaaaaaaattgaccca ttgttccataccgtcgaggcgggggtatgtaaattggacccagagaaaac tcatcaggctgttgaaaaacgcttgggtgggccattaaatgaactgagtc aacgctatgccaagcccttgccctgatgggcgaggtgctgaattttcg gcctcaccttattgcaactcactgcaacagaaaggaaaaacctgtgattt tgcgacttttgcagcaaatgaaatcgaggtaaataaagaagggacaaaag tctcactgagtgggccattggcgctatcatcgacattaggtgaaattttc ctattacaaaattcacaggccatgccagatgtcgcctggaaccgtctcag cggtgaagaaaattggatttcattattgtcactgcataatgcacagttcg atttgatggccaaaacccttatatcgcccggcataaaggaactccgttg ttgcaacaaattgatacggcattagtgttgcaacgtgatgctcaggggca aacactgccgctgtcaccgcaaaccaaattgctgttcctcgggggacatg acaccaatattgccaatattgcgggtatgttaggggccaattggcaatta ccgcagcaacctgataataccccgccaggcggagggctagtctttgagct atggcagaatccggataaccatcaacgctatgtggcggtgaaaatgttct atcaaacgatggagcagttgcgcaatgcagataagttagatttgaaaaac aacccggcaagaattgttcccattgctattgaagggtgtgaaaacgaggg tgataacaaactttgtcagcttgaaacgttccaaaagaaagtcgcccaag tgatcgagccagcctgccatatttaa
```

According to the present invention, said phytase variants YkAPPA having improved pepsin resistance and increased catalytic efficiency are obtained by mutation at the 162$^{th}$ site of Leucine into glycine or alanine, or the 230$^{th}$ site of glutamic acid into glycine, alanine, serine, threonine, aspartic acid, proline, or arginine for phytase with amino acid as set forth in SEQ ID NO.1.

According to embodiment of the present invention, the phytase variant YkAPPA-L162G with amino acid sequence as set forth in SEQ ID NO.3 is obtained by mutation at the 162$^{th}$ site of Leucine into glycine for phytase with amino acid as set forth in SEQ ID NO.1.

According to embodiment of the present invention, the phytase variant YkAPPA-L162A with amino acid sequence as set forth in SEQ ID NO.4 is obtained by mutation at the 162$^{th}$ site of Leucine into alanine for phytase with amino acid as set forth in SEQ ID NO.1.

According to embodiment of the present invention, the phytase variant YkAPPA-E230G with amino acid sequence as set forth in SEQ ID NO.5 is obtained by mutation at the 230$^{th}$ site of glutamic acid into glycine for phytase with amino acid as set forth in SEQ ID NO.1.

According to embodiment of the present invention, the phytase variant YkAPPA-E230A with amino acid sequence as set forth in SEQ ID NO.6 is obtained by mutation at the $230^{th}$ site of glutamic acid into alanine for phytase with amino acid as set forth in SEQ ID NO.1.

According to embodiment of the present invention, the phytase variant YkAPPA-E230S with amino acid sequence as set forth in SEQ ID NO.7 is obtained by mutation at the $230^{th}$ site of glutamic acid into serine for phytase with amino acid as set forth in SEQ ID NO.1.

According to embodiment of the present invention, the phytase variant YkAPPA-E230T with amino acid sequence as set forth in SEQ ID NO.8 is obtained by mutation at the $230^{th}$ site of glutamic acid into threonine for phytase with amino acid as set forth in SEQ ID NO.1.

According to embodiment of the present invention, the phytase variant YkAPPA-E230D with amino acid sequence as set forth in SEQ ID NO.9 is obtained by mutation at the $230^{th}$ site of glutamic acid into aspartic acid for phytase with amino acid as set forth in SEQ ID NO.1.

According to embodiment of the present invention, the phytase variant YkAPPA-E230P with amino acid sequence as set forth in SEQ ID NO.10 is obtained by mutation at the $230^{th}$ site of glutamic acid into proline for phytase with amino acid as set forth in SEQ ID NO.1.

According to embodiment of the present invention, the phytase variant YkAPPA-E230R with amino acid sequence as set forth in SEQ ID NO.11 is obtained by mutation at the $230^{th}$ site of arginine into proline for phytase with amino acid as set forth in SEQ ID.

Another aspect of the invention is to provide a gene encoding the above phytase variants having improved pepsin resistance and increased catalytic efficiency, with nucleotide sequence as set forth in SEQ ID NO.12, SEQ ID NO.13, SEQ ID NO.14, SEQ ID NO.15, SEQ ID NO.16, SEQ ID NO.17, SEQ ID NO.18, SEQ ID NO.19, SEQ ID NO.20 respectively.

According to embodiment of the present invention, the gene encoding the phytase variant YkAPPA-L162G has nucleotide sequence as set forth in SEQ ID NO.12.

According to embodiment of the present invention, the gene encoding the phytase variant YkAPPA-L162A has nucleotide sequence as set forth in SEQ ID NO.13.

According to embodiment of the present invention, the gene encoding the phytase variant YkAPPA-E230G has nucleotide sequence as set forth in SEQ ID NO.14.

According to embodiment of the present invention, the gene encoding the phytase variant YkAPPA-E230A has nucleotide sequence as set forth in SEQ ID NO.15.

According to embodiment of the present invention, the gene encoding the phytase variant YkAPPA-E230S has nucleotide sequence as set forth in SEQ ID NO.16.

According to embodiment of the present invention, the gene encoding the phytase variant YkAPPA-E230T has nucleotide sequence as set forth in SEQ ID NO.17.

According to embodiment of the present invention, the gene encoding the phytase variant YkAPPA-E230D has nucleotide sequence as set forth in SEQ ID NO.18.

According to embodiment of the present invention, the gene encoding the phytase variant YkAPPA-E230P has nucleotide sequence as set forth in SEQ ID NO.19.

According to embodiment of the present invention, the gene encoding the phytase variant YkAPPA-E230R has nucleotide sequence as set forth in SEQ ID NO.20.

Another aspect of the invention is to provide a recombinant vector comprising polynucleotides encoding above phytase variants having improved pepsin resistance and increased catalytic efficiency, and preferably provide a recombinant *E coli*. expression vector comprising the genes encoding phytase variants inserted between sites EcoRI and NotI as so to be controlled under the promoter T7-lac.

Yet another aspect of the invention is to provide a recombinant host cell comprising polynucleotides encoding above phytase variants, and preferably provide a recombinant *E coli* host, recombinant *E coli* BL21 (DE3).

Phytase variants of the present invention have the improved pepsin resistance wherein the phytase variants YkAPPA-L162G, YkAPPA-E230G and YkAPPA-E230A have the catalytic efficiency increased to 2.1 times of that of the wild phytase, in the benefit of the development of economical feed enzyme industry.

BRIEF DESCRIPTIONS OF THE DRAWINGS

EMBODIMENT

Figure 1:
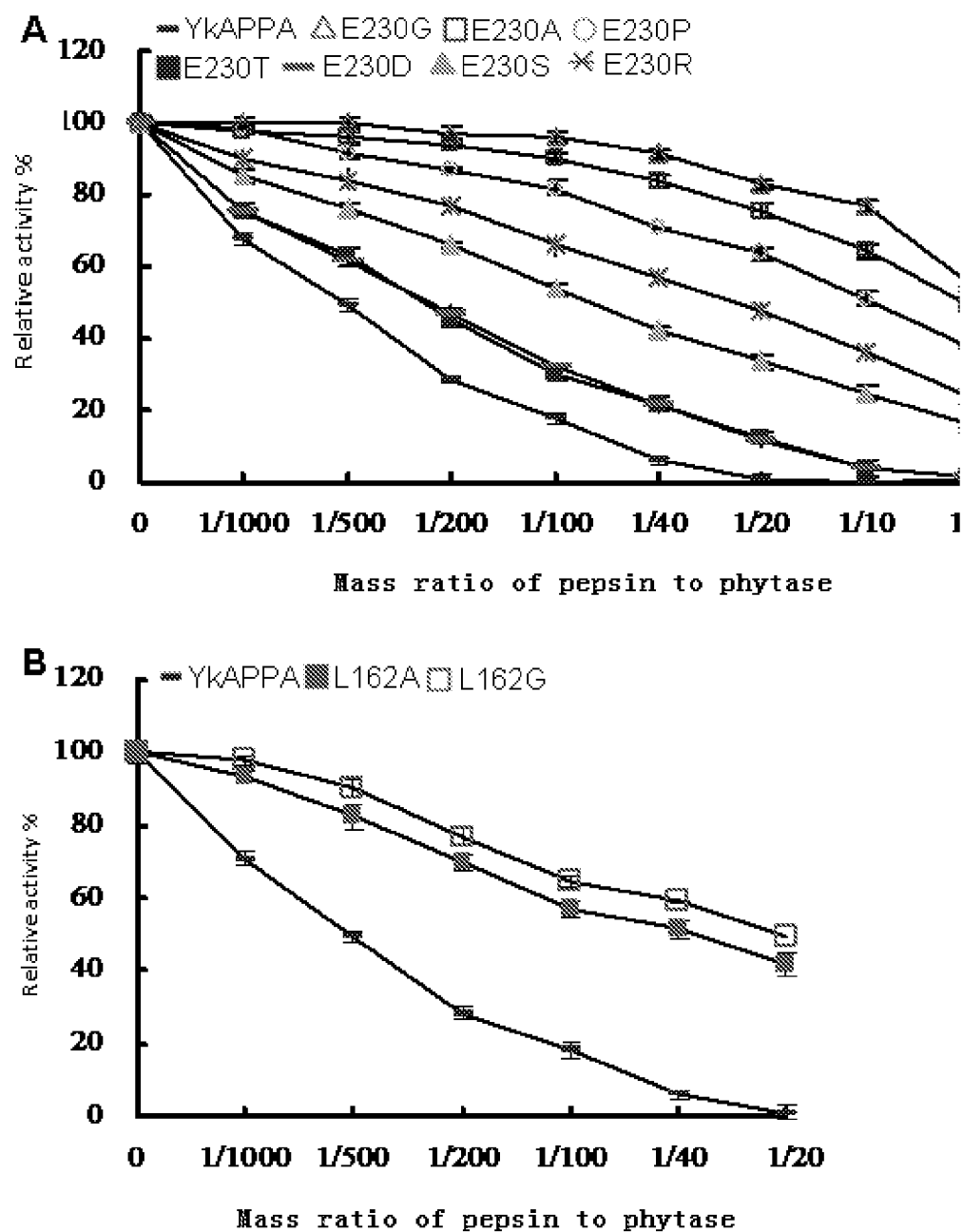
FIG. 1 shows the comparison of effect of pepsin on activity of the modified phytase and the wild phytase.

The present invention is further illustrated with reference to the following Examples and the appended drawings, which should by no means be construed as limitations of the present invention.

Test Materials and Reagents

1. Strains and vectors: Expression vetor pET-22b (+) and host strain BL21 (DE3) (Novagen)

2. Enzymes and other biochemical reagents: restriction endonucleases (TaKaRa), ligase (Invitrogen), and pepsin p0685 (Sigma).

3. Medium:

*E. coli*. LB medium: 1% of peptone, 0.5% of yeast extract, and 1% of NaCl, natural pH.

Suitable biology laboratory methods not particularly mentioned in the examples as below can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other kit laboratory manuals.

Example 1 Introduction of the Mutant Site to Wild Phytase

Gene encoding phytase YkAPPA having the nucleotide sequence as set in SEQ ID NO. 2 from *Y. kristensenii* was performed with site-directed mutagenesis by Overlap PCR to obtain genes encodng the phytase variants YeAPPA-L162G, YeAPPA-L162A, YeAPPA-E230G, YkAPPA-E230A, YkAPPA-E230S, YkAPPA-E230T, YkAPPA-E230D, YkAPPA-E230P, and YkAPPA-E230R, respectively. Overlap PCR was performed as being kept at 95° C. for 5 min, followed by 30 cycles of 94° C. for 30 sec, 55° C. for 30 sec, and 72° C. for 30-90 sec, and keep 72° C. for 10 min, using 20 mutation primers including the upper primer Ye-F and the reverse primer Ye-R for amplifying the full length of mutant gene, and the primers comprising the EcoRI and NotI sites marked in Italics or the mutant nucleotides marked in underlined for site-directed mutagenesis showed as below.

```
Yk-F:   5'-cgcgaattcgcaccgcttgcagcacaatctac-3'

Yk-R:   5'-gatgcggccgcttaaatatggcaggctggctcg-3'

L162G-F: 5'-cggggtatgtaaaggcgacccagagaaaac-3'

L162G-R: 5'-gttttctctgggtcgcctttacataccccg-3'

L162A-F: 5'-cggggtatgtaaagcgacccagagaaaac-3'

L162A-R: 5'-gttactctgggtcgcttacataccccg-3'

E230G-F: 5'-tcgaggtaaataaaggcgggacaaaagtctc-3'

E230G-R: 5'-gagacttttgtcccgcctttatttacctcga-3'

E230A-F: 5'-tcgaggtaaataaagcgggacaaaagtctc-3'

E230A-R: 5'-gagacttttgtcccgctttatttacctcga-3'

E230S-F: 5'-tcgaggtaaataaatctgggacaaaagtctc-3'

E230S-R: 5'-gagacttttgtcccagattatttacctcga-3'

E230T-F: 5'-tcgaggtaaataaaaccgggacaaaagtctc-3'

E230T-R: 5'-gagacttttgtcccggttttatttacctcga-3'

E230D-F: 5'-tcgaggtaaataaagatggggacaaaagtctc-3'

E230D-R: 5'-gagacttttgtcccatctttatttacctcga-3'

E230P-F: 5'-tcgaggtaaataaaccgggacaaaagtctc-3'

E230P-R: 5'-gagacttttgtcccggtttatttacctcga-3'

E230R-F: 5'-tcgaggtaaataaacgtgggacaaaagtctc-3'

E230R-R: 5'-gagacttttgtcccacgtttatttacctcga-3'
```

The modified gene was recovered, connected with the vector pEASY-T3, and sequenced.

Example 2 Expressing the Phytase in *E coli*

The modified genes encoding the phytase variants were inserted into expression vector pET-22b (+), and transformed into *E coli*. Strain BL21 (DE3), which were induced by IPTG in 1 mM, cultivated for 5 h at 24° C. to express the phytase, followed by being purified by columns Ni-NTA and DEAE to obtain the mutant protein with the same molecular weight as that of the wild.

Example 3 Measuring the Activity of the Phytase Variants

Measuring Effect of Pepsin on the Enzyme Activity of the Phytase Variants 1 unit of phytase activity is determined to be the enzyme amount releasing 1 μmol of phosphate for 1 minute. The absolute value of the measured phytase activity may be calculated based on the standard curve of inorganic phosphate in dilution.

The effect of pepsin on the activity of the purified mutant phytase was determined by detecting the remaining activity after being treated in pH 2 for 2 hours with the different concentrations of pepsin in a mass ratio to phytase ranging from 1/1000 to 1/1. The activity of phytase was detected by ferric molybdenum sulfate blue method by adding 50 ul of phytase solution to 950 ul of sodium phytate substrate in 1.5 mmol/L to react for 30 min at 37° C., followed by adding 1 mL of 10% (m/v) TCA to stop the reaction, and 2 mL of developing color reagent. After developing, OD is measured at 700 nm to calculate the phytase activity. As showed in "A" and "B" of FIG. 1, in the case of the ratio pepsin to phytase ranging from 1/1000 to 1/20, the phytase variants remain far more enzyme activity after being treated for 2 h in different concentration of pepsin, than that of the wild phytase, wherein the retained activity of the phytase variants YkAPPA-E230G, YkAPPA-E230A, YkAPPA-L162G, YkAPPA-L162A, YkAPPA-E230S, YkAPPA-E230D and YkAPPA-E230T were 83%, 76%, 50%, 42%, 34%, 12% and more than 12% in order, and the retained activity of the phytase variants YkAPPA-E230P and YkAPPA-E230R with the strong rigid side chains were more than 64% and more than 49% in order, but the wild phytase almost lost activity, demonstrating that pepsin resistance of phytase variants were improved.

Measuring the Optimal pH and Optimal Temperature

The purified phytase variants were performed the enzymatic reactions in the substrate solutions with the different pHs using 0.1 mol/L of Glycine-HCl buffer (pH1.0~3.0), 0.1 mol/L of acetic acid-sodium acetate buffer (pH3~6), 0.1 mol/L of Tris-Hcl buffer (pH6~8) and 0.1 mol/L of glycine-sodium hydroxide buffer (pH8~12.0) at 37° C. to deterimine the optimal pH. As showed in Table 1, the optimal pH values of the eights phytase variants were pH 4.5 similar f to that of the wild enzyme, other than the optimal pH of the phytase variant YkAPPA-E230R decreased 0.5 pH units. And, the phytase variants YkAPPA-E230G, YkAPPA-E230A, YkAPPA-E230R, YkAPPA-L162G, and YkAPPA-L162A were more acid stable than the wild phytase, wherein the phytase variants YkAPPA-E230G, YkAPPA-E230A, and YkAPPA-E230R can retain more than 85% of enzyme activity, but the wild phytase only retained 64% of enzyme activity after being treated in pH 1.0 to 1.5 for 1 hour. And, phytase variants YkAPPA-E230P, YkAPPA-E230S, YkAPPA-E230T, and YkAPPA-E230D had the similar acid stability as the wild phytase.

TABLE 1

Comparison of the effect temperature and pH on the activity and stability of the modified phytase and the wild phytase

| Variants | Optimal pH | Optimal temperature | pH stability of the phytase after being treated in different pHs for 1 h | Thermostability of phytase kept for 30 min at 60° C. |
|---|---|---|---|---|
| YkAPPA | 4.5 | 55° C. | pH 1-1.5, 64-77%; pH 2-10, >91% | 16% |
| YkAPPA-E230G | 4.5 | 55° C. | pH 1-1.5, >92%; pH 2-10, >99% | 35% |
| YkAPPA-E230A | 4.5 | 55° C. | pH 1-1.5, >87%; pH 2-10, >99% | 16% |
| YkAPPA-E230P | 4.5 | 60° C. | pH 1-1.5, <78%; pH 2-10, >88% | 42% |
| YkAPPA-E230R | 4.0 | 55° C. | pH 1-1.5, >87%; pH 2-10, >95% | 23% |
| YkAPPA-E230S | 4.5 | 55° C. | pH 1-1.5, <79%; pH 2-10, >89% | 34% |
| YkAPPA-E230T | 4.5 | 55° C. | pH 1-1.5, <78%; pH 2-10, >91% | 33% |
| YkAPPA-E230D | 4.5 | 55° C. | pH 1-1.5, <77%; pH 2-10, >91% | 17% |
| YkAPPA-L162G | 4.5 | 55° C. | pH 1-1.5, >90%; pH 2-10 > 100% | 17% |
| YkAPPA-L162A | 4.5 | 55° C. | pH 1-1.5, >85%; pH 2-10 > 93% | 17% |

Measuring Kinetic Parameter of the Phytase Variants

The activity of phytase was measured with sodium phytate as substrate in different concentrations of 0.0625 mmol/L, 0.1 mmol/L, 0.125 mmol/L, 0.2 mmol/L, 0.25 mmol/L, 0.5 mmol/L, 1.0 mmol/L and 1.5 mmol/L at the optimal temperature and pH, followed by calculating the values of $k_m$ and $V_{max}$ by double reciprocal method for Michaelis equation, and $K_{cat}$ according to the theoretical molecular weight. As showed in Table 2, the affinity ($k_m$) for each of phytase variants to substrates was almost similar to that for the wild phytase. Reaction rate $V_{max}$ and conversion rate $K_{cat}$ of the phytase variant YkAPPA-E230G are greatly increased to 1.9 times of that of the wild phytase, and catalytic efficiency $K_{cat}/k_m$ was 2.1 times of that of the wild phytase, and reaction rate $V_{max}$ and conversion rate $K_{cat}$ of the phytase variant YkAPPA-L162G was increased to 1.6 to 1.8 times of that of the wild phytase. Reaction rate $V_{max}$, conversion rate $K_{cat}$ of the phytase variant YkAPPA-E230A was 1.3 times of those of the wild phytase. And, the catalytic properties including reaction rate, turnover rate and catalytic efficiency of the other phytase variants were similar to those of the wild phytase.

TABLE 2

Comparison of the enzymatic properties of the modified phytase and the wild phytase

| Variants | Km (mM) | Vmax (U mg$^{-1}$) | Kcat (S$^{-1}$) | Kcat/Km (S$^{-1}$ mM$^{-1}$) |
|---|---|---|---|---|
| YkAPPA | 0.09 | 3554 | 2719 | 29423 |
| YkAPPA-E230G | 0.10 | 7097 | 5429 | 61690 |
| YkAPPA-E230A | 0.09 | 4533 | 3468 | 37685 |
| YkAPPA-E230P | 0.08 | 3177 | 2430 | 29833 |
| YkAPPA-E230R | 0.11 | 4329 | 3312 | 29883 |
| YkAPPA-E230S | 0.09 | 3795 | 2903 | 29298 |
| YkAPPA-E230T | 0.08 | 3247 | 2484 | 29767 |
| YkAPPA-E230D | 0.09 | 3587 | 2744 | 29088 |
| YkAPPA-L162G | 0.09 | 6321 | 4836 | 46084 |
| YkAPPA-L162A | 0.10 | 3917 | 2996 | 29537 |

Example 3 Measuring Activity of the Phytase Variants

Figure 2:
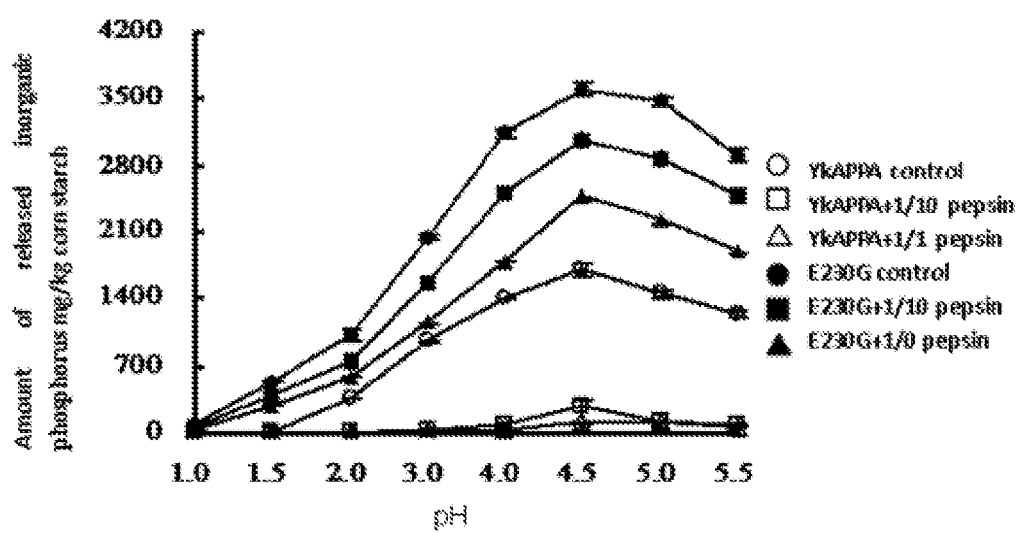
FIG. 2 shows the comparison of the hydrolysis ability of the modified phytase and the wild phytase.

The gastrointestinal environment of animals was simulated with different pH ranging from 1.0 to 5.5 and in the different ratio of pepsin to phytase ranging from 1/100 to 1/1, so as to determine hydrolysis ability of the variant YkAPPA-E230G taking corn starch as a substrate. As showed in FIG. 2, for the variant YkAPPA-E230G, the amount of inorganic phosphorus released by hydrolyzing the corn starch was the most which was 2 times of that of the wild phytase without adding pepsin, and increased to 11 times and 24 times when adding pepsin in a ratio of 1/10 and 1/1 respectively, in case of pH 4.5.

The invention claimed is:

1. A Phytase YkAPPA variant having the amino acid sequence obtained by substituting glutamic acid at the 230$^{th}$ site of the sequence of SEQ ID NO:1 with glycine, proline, or arginine, and having improved pepsin resistance and increased catalytic efficiency.

2. A polynucleotide encoding the phytase YkAPPA variant of claim 1.

3. The polynucleotide according to claim 2, wherein said polynucleotide is selected from the group consisting of SEQ ID NO:14, SEQ ID NO:19 or SEQ ID NO:20.

4. A DNA construct comprising the polynucleotide of claim 2.

5. A recombinant host cell comprising the polynucleotide of claim 2.

6. A method of producing a phytase variant comprising the steps of: i.) transforming the host cell with the DNA construct of claim 4 to obtain a recombinant host cell; ii.) cultivating the recombinant host cell to produce the supernatant containing phytase variant; and iii.) recovering the said phytase variant.

* * * * *

SEQUENCE LISTING

<160> NUMBER OF SEQ ID NOS: 20

<210> SEQ ID NO 1
<211> LENGTH: 441
<212> TYPE: PRT
<213> ORGANISM: Yersinia enterocolitica

<400> SEQUENCE: 1

Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
                20                  25                  30

Gly Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
        50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
                100                 105                 110

Gln Ala Asp Val Asp Gln Arg Thr Arg Leu Thr Gly Gln Ala Phe Leu
            115                 120                 125

Asp Gly Ile Ala Pro Asp Cys Gly Leu Lys Val His Tyr Gln Ala Asp
        130                 135                 140

Leu Lys Lys Ile Asp Pro Leu Phe His Thr Val Glu Ala Gly Val Cys
145                 150                 155                 160

Lys Leu Asp Pro Glu Lys Thr His Gln Ala Val Glu Lys Arg Leu Gly
                165                 170                 175

-continued

```
Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Glu Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
        435                 440
```

<210> SEQ ID NO 2
<211> LENGTH: 1326
<212> TYPE: DNA
<213> ORGANISM: Yersinia kristensenii

<400> SEQUENCE: 2

```
atgacaatag caaaagaata tctgcggtta tccatactca ctttggtgct cagtagtttt      60
acgctaagtg ctgcaccgct tgcagcacaa tctaccggtt acactttgga gcgcgtggtg     120
attttgagcc gccacggtgt tcgttccccg acgaaacaaa cacagttaat gaatgatgtt     180
acaccggaca aatggccaca atggccagta aaagcgggct atttaacgcc gcgaggggca     240
ggattagtca ctttaatggg cgggttctat ggtgattatt tccgcagcta tgggttgtta     300
ccggcggggt gcccggcaga cgaatccatc tatgtgcaag ctgatgttga ccaacgtacc     360
cgcttaaccg ggcaggcatt tctggacggt atagccccgg attgcggcct gaaagtacat     420
tatcaagctg atttgaaaaa aattgaccca ttgttccata ccgtcgaggc gggggtatgt     480
aaattggacc cagagaaaac tcatcaggct gttgaaaaac gcttgggtgg gccattaaat     540
gaactgagtc aacgctatgc caagcccttt gccctgatgg gcgaggtgct gaatttttcg     600
```

```
gcctcacctt attgcaactc actgcaacag aaaggaaaaa cctgtgattt tgcgactttt      660
gcagcaaatg aaatcgaggt aaataaagaa gggacaaaag tctcactgag tgggccattg      720
gcgctatcat cgacattagg tgaaattttc ctattacaaa attcacaggc catgccagat      780
gtcgcctgga accgtctcag cggtgaagaa aattggattt cattattgtc actgcataat      840
gcacagttcg atttgatggc caaaacccct tatatcgccc ggcataaagg aactccgttg      900
ttgcaacaaa ttgatacggc attagtgttg caacgtgatg ctcaggggca aacactgccg      960
ctgtcaccgc aaaccaaatt gctgttcctc gggggacatg acaccaatat tgccaatatt     1020
gcgggtatgt tagggccaa ttggcaatta ccgcagcaac tgataatac cccgccaggc      1080 ggagggctag tctttgagct atggcagaat ccggataacc atcaacgcta tgtggcggtg     1140
aaaatgttct atcaaacgat ggagcagttg cgcaatgcag ataagttaga tttgaaaaac     1200
aacccggcaa gaattgttcc cattgctatt gaagggtgtg aaaacgaggg tgataacaaa     1260
ctttgtcagc ttgaaacgtt ccaaaagaaa gtcgcccaag tgatcgagcc agcctgccat     1320
atttaa                                                                1326
```

<210> SEQ ID NO 3
<211> LENGTH: 441
<212> TYPE: PRT
<213> ORGANISM: Artificial Sequence
<220> FEATURE:
<223> OTHER INFORMATION: VARIANT

<400> SEQUENCE: 3

```
Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
145                 150                 155                 160

Lys Gly Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Glu Gly Thr Lys Val Ser Leu Ser Gly Pro Leu
```

```
                225                 230                 235                 240
Ala Leu Ser Ser Thr Leu Gly Glu Ile Phe Leu Leu Gln Asn Ser Gln
                    245                 250                 255

Ala Met Pro Asp Val Ala Trp Asn Arg Leu Ser Gly Glu Glu Asn Trp
                260                 265                 270

Ile Ser Leu Leu Ser Leu His Asn Ala Gln Phe Asp Leu Met Ala Lys
                    275                 280                 285

Thr Pro Tyr Ile Ala Arg His Lys Gly Thr Pro Leu Leu Gln Gln Ile
                290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                    325                 330                 335

Ile Ala Asn Ile Ala Gly Met Leu Gly Ala Asn Trp Gln Leu Pro Gln
                340                 345                 350

Gln Pro Asp Asn Thr Pro Pro Gly Gly Gly Leu Val Phe Glu Leu Trp
                    355                 360                 365

Gln Asn Pro Asp Asn His Gln Arg Tyr Val Ala Val Lys Met Phe Tyr
                370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                    405                 410                 415

Gly Asp Asn Lys Leu Cys Gln Leu Glu Thr Phe Gln Lys Lys Val Ala
                420                 425                 430

Gln Val Ile Glu Pro Ala Cys His Ile
                    435                 440

<210> SEQ ID NO 4
<211> LENGTH: 441
<212> TYPE: PRT
<213> ORGANISM: Artificial Sequence
<220> FEATURE:
<223> OTHER INFORMATION: VARIANT

<400> SEQUENCE: 4

Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
                20                  25                  30

Gly Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
        50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
```

```
        145                 150                 155                 160
Lys Ala Asp Pro Glu Lys Thr His Gln Ala Val Glu Lys Arg Leu Gly
                    165                 170                 175

Gly Pro Leu Asn Glu Leu Ser Gln Arg Tyr Ala Lys Pro Phe Ala Leu
                180                 185                 190

Met Gly Glu Val Leu Asn Phe Ser Ala Ser Pro Tyr Cys Asn Ser Leu
            195                 200                 205

Gln Gln Lys Gly Lys Thr Cys Asp Phe Ala Thr Phe Ala Ala Asn Glu
        210                 215                 220

Ile Glu Val Asn Lys Glu Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
        435                 440

<210> SEQ ID NO 5
<211> LENGTH: 441
<212> TYPE: PRT
<213> ORGANISM: Artificial Sequence
<220> FEATURE:
<223> OTHER INFORMATION: VARIANT

<400> SEQUENCE: 5

Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
                20                  25                  30

Gly Tyr Thr Leu Glu Arg Val Ile Leu Ser Arg His Gly Val Arg
            35                  40                  45

Ser Pro Thr Lys Gln Thr Gln Leu Met Asn Asp Val Thr Pro Asp Lys
        50                  55                  60

Trp Pro Gln Trp Pro Val Lys Ala Gly Tyr Leu Thr Pro Arg Gly Ala
```

```
                65                  70                  75                  80
Gly Leu Val Thr Leu Met Gly Gly Phe Tyr Gly Asp Tyr Phe Arg Ser
                    85                  90                  95
Tyr Gly Leu Leu Pro Ala Gly Cys Pro Ala Asp Glu Ser Ile Tyr Val
                100                 105                 110
Gln Ala Asp Val Asp Gln Arg Thr Arg Leu Thr Gly Gln Ala Phe Leu
                115                 120                 125
Asp Gly Ile Ala Pro Asp Cys Gly Leu Lys Val His Tyr Gln Ala Asp
130                 135                 140
Leu Lys Lys Ile Asp Pro Leu Phe His Thr Val Glu Ala Gly Val Cys
145                 150                 155                 160
Lys Ala Asp Pro Glu Lys Thr His Gln Ala Val Glu Lys Arg Leu Gly
                165                 170                 175
Gly Pro Leu Asn Glu Leu Ser Gln Arg Tyr Ala Lys Pro Phe Ala Leu
                180                 185                 190
Met Gly Glu Val Leu Asn Phe Ser Ala Ser Pro Tyr Cys Asn Ser Leu
                195                 200                 205
Gln Gln Lys Gly Lys Thr Cys Asp Phe Ala Thr Phe Ala Ala Asn Glu
                210                 215                 220
Ile Glu Val Asn Lys Gly Gly Thr Lys Val Ser Leu Ser Gly Pro Leu
225                 230                 235                 240
Ala Leu Ser Ser Thr Leu Gly Glu Ile Phe Leu Leu Gln Asn Ser Gln
                245                 250                 255
Ala Met Pro Asp Val Ala Trp Asn Arg Leu Ser Gly Glu Glu Asn Trp
                260                 265                 270
Ile Ser Leu Leu Ser Leu His Asn Ala Gln Phe Asp Leu Met Ala Lys
                275                 280                 285
Thr Pro Tyr Ile Ala Arg His Lys Gly Thr Pro Leu Leu Gln Gln Ile
                290                 295                 300
Asp Thr Ala Leu Val Leu Gln Arg Asp Ala Gln Gly Gln Thr Leu Pro
305                 310                 315                 320
Leu Ser Pro Gln Thr Lys Leu Leu Phe Leu Gly Gly His Asp Thr Asn
                325                 330                 335
Ile Ala Asn Ile Ala Gly Met Leu Gly Ala Asn Trp Gln Leu Pro Gln
                340                 345                 350
Gln Pro Asp Asn Thr Pro Pro Gly Gly Leu Val Phe Glu Leu Trp
                355                 360                 365
Gln Asn Pro Asp Asn His Gln Arg Tyr Val Ala Val Lys Met Phe Tyr
                370                 375                 380
Gln Thr Met Glu Gln Leu Arg Asn Ala Asp Lys Leu Asp Leu Lys Asn
385                 390                 395                 400
Asn Pro Ala Arg Ile Val Pro Ile Ala Ile Glu Gly Cys Glu Asn Glu
                405                 410                 415
Gly Asp Asn Lys Leu Cys Gln Leu Glu Thr Phe Gln Lys Lys Val Ala
                420                 425                 430
Gln Val Ile Glu Pro Ala Cys His Ile
                435                 440

<210> SEQ ID NO 6
<211> LENGTH: 441
<212> TYPE: PRT
<213> ORGANISM: Artificial Sequence
<220> FEATURE:
<223> OTHER INFORMATION: VARIANT
```

<400> SEQUENCE: 6

```
Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
145                 150                 155                 160

Lys Ala Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Ala Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415
```

```
Gly Asp Asn Lys Leu Cys Gln Leu Glu Thr Phe Gln Lys Lys Val Ala
                420                 425                 430

Gln Val Ile Glu Pro Ala Cys His Ile
        435                 440
```

<210> SEQ ID NO 7
<211> LENGTH: 441
<212> TYPE: PRT
<213> ORGANISM: Artificial Sequence
<220> FEATURE:
<223> OTHER INFORMATION: VARIANT

<400> SEQUENCE: 7

```
Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
                20                  25                  30

Gly Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
    50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
145                 150                 155                 160

Lys Ala Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Ser Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335
```

```
Ile Ala Asn Ile Ala Gly Met Leu Gly Ala Asn Trp Gln Leu Pro Gln
                340                 345                 350

Gln Pro Asp Asn Thr Pro Pro Gly Gly Leu Val Phe Glu Leu Trp
            355                 360                 365

Gln Asn Pro Asp Asn His Gln Arg Tyr Val Ala Val Lys Met Phe Tyr
            370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
            435                 440

<210> SEQ ID NO 8
<211> LENGTH: 441
<212> TYPE: PRT
<213> ORGANISM: Artificial Sequence
<220> FEATURE:
<223> OTHER INFORMATION: VARIANT

<400> SEQUENCE: 8

Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
145                 150                 155                 160

Lys Ala Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Thr Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255
```

```
Ala Met Pro Asp Val Ala Trp Asn Arg Leu Ser Gly Glu Glu Asn Trp
        260                 265                 270
Ile Ser Leu Leu Ser Leu His Asn Ala Gln Phe Asp Leu Met Ala Lys
    275                 280                 285
Thr Pro Tyr Ile Ala Arg His Lys Gly Thr Pro Leu Leu Gln Gln Ile
290                 295                 300
Asp Thr Ala Leu Val Leu Gln Arg Asp Ala Gln Gly Gln Thr Leu Pro
305                 310                 315                 320
Leu Ser Pro Gln Thr Lys Leu Leu Phe Leu Gly Gly His Asp Thr Asn
            325                 330                 335
Ile Ala Asn Ile Ala Gly Met Leu Gly Ala Asn Trp Gln Leu Pro Gln
        340                 345                 350
Gln Pro Asp Asn Thr Pro Pro Gly Gly Gly Leu Val Phe Glu Leu Trp
    355                 360                 365
Gln Asn Pro Asp Asn His Gln Arg Tyr Val Ala Val Lys Met Phe Tyr
370                 375                 380
Gln Thr Met Glu Gln Leu Arg Asn Ala Asp Lys Leu Asp Leu Lys Asn
385                 390                 395                 400
Asn Pro Ala Arg Ile Val Pro Ile Ala Ile Glu Gly Cys Glu Asn Glu
                405                 410                 415
Gly Asp Asn Lys Leu Cys Gln Leu Glu Thr Phe Gln Lys Lys Val Ala
            420                 425                 430
Gln Val Ile Glu Pro Ala Cys His Ile
        435                 440

<210> SEQ ID NO 9
<211> LENGTH: 441
<212> TYPE: PRT
<213> ORGANISM: Artificial Sequence
<220> FEATURE:
<223> OTHER INFORMATION: VARIANT

<400> SEQUENCE: 9

Met Thr Ile Ala Lys Glu Tyr Leu Arg Leu Ser Ile Leu Thr Leu Val
1               5                   10                  15
Leu Ser Ser Phe Thr Leu Ser Ala Ala Pro Leu Ala Ala Gln Ser Thr
            20                  25                  30
Gly Tyr Thr Leu Glu Arg Val Val Ile Leu Ser Arg His Gly Val Arg
        35                  40                  45
Ser Pro Thr Lys Gln Thr Gln Leu Met Asn Asp Val Thr Pro Asp Lys
    50                  55                  60
Trp Pro Gln Trp Pro Val Lys Ala Gly Tyr Leu Thr Pro Arg Gly Ala
65                  70                  75                  80
Gly Leu Val Thr Leu Met Gly Gly Phe Tyr Gly Asp Tyr Phe Arg Ser
                85                  90                  95
Tyr Gly Leu Leu Pro Ala Gly Cys Pro Ala Asp Glu Ser Ile Tyr Val
            100                 105                 110
Gln Ala Asp Val Asp Gln Arg Thr Arg Leu Thr Gly Gln Ala Phe Leu
        115                 120                 125
Asp Gly Ile Ala Pro Asp Cys Gly Leu Lys Val His Tyr Gln Ala Asp
    130                 135                 140
Leu Lys Lys Ile Asp Pro Leu Phe His Thr Val Glu Ala Gly Val Cys
145                 150                 155                 160
Lys Ala Asp Pro Glu Lys Thr His Gln Ala Val Glu Lys Arg Leu Gly
                165                 170                 175
```

```
Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
            195                 200                 205

Gln Gln Lys Gly Lys Thr Cys Asp Phe Ala Thr Phe Ala Ala Asn Glu
210                 215                 220

Ile Glu Val Asn Lys Asp Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
            275                 280                 285

Thr Pro Tyr Ile Ala Arg His Lys Gly Thr Pro Leu Leu Gln Gln Ile
            290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Leu Val Phe Glu Leu Trp
            355                 360                 365

Gln Asn Pro Asp Asn His Gln Arg Tyr Val Ala Val Lys Met Phe Tyr
            370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
            435                 440

<210> SEQ ID NO 10
<211> LENGTH: 441
<212> TYPE: PRT
<213> ORGANISM: Artificial Sequence
<220> FEATURE:
<223> OTHER INFORMATION: VARIANT

<400> SEQUENCE: 10

Met Thr Ile Ala Lys Glu Tyr Leu Arg Leu Ser Ile Leu Thr Leu Val
1               5                   10                  15

Leu Ser Ser Phe Thr Leu Ser Ala Ala Pro Leu Ala Ala Gln Ser Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
                85                  90                  95
```

```
Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
            115                 120                 125

Asp Gly Ile Ala Pro Asp Cys Gly Leu Lys Val His Tyr Gln Ala Asp
        130                 135                 140

Leu Lys Lys Ile Asp Pro Leu Phe His Thr Val Glu Ala Gly Val Cys
145                 150                 155                 160

Lys Ala Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
        210                 215                 220

Ile Glu Val Asn Lys Pro Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
        290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Leu Val Phe Glu Leu Trp
        355                 360                 365

Gln Asn Pro Asp Asn His Gln Arg Tyr Val Ala Val Lys Met Phe Tyr
370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
        435                 440

<210> SEQ ID NO 11
<211> LENGTH: 441
<212> TYPE: PRT
<213> ORGANISM: Artificial Sequence
<220> FEATURE:
<223> OTHER INFORMATION: VARIANT

<400> SEQUENCE: 11

Met Thr Ile Ala Lys Glu Tyr Leu Arg Leu Ser Ile Leu Thr Leu Val
1               5                   10                  15
```

```
Leu Ser Ser Phe Thr Leu Ser Ala Ala Pro Leu Ala Ala Gln Ser Thr
            20                  25                  30

Gly Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
50                  55                  60

Trp Pro Gln Trp Pro Val Lys Ala Gly Tyr Leu Thr Pro Arg Gly Ala
65                  70                  75                  80

Gly Leu Val Thr Leu Met Gly Gly Phe Tyr Gly Asp Tyr Phe Arg Ser
            85                  90                  95

Tyr Gly Leu Leu Pro Ala Gly Cys Pro Ala Asp Glu Ser Ile Tyr Val
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Ile Asp Pro Leu Phe His Thr Val Glu Ala Gly Val Cys
145                 150                 155                 160

Lys Ala Asp Pro Glu Lys Thr His Gln Ala Val Glu Lys Arg Leu Gly
                165                 170                 175

Gly Pro Leu Asn Glu Leu Ser Gln Arg Tyr Ala Lys Pro Phe Ala Leu
            180                 185                 190

Met Gly Glu Val Leu Asn Phe Ser Ala Ser Pro Tyr Cys Asn Ser Leu
        195                 200                 205

Gln Gln Lys Gly Lys Thr Cys Asp Phe Ala Thr Phe Ala Ala Asn Glu
    210                 215                 220

Ile Glu Val Asn Lys Arg Gly Thr Lys Val Ser Leu Ser Gly Pro Leu
225                 230                 235                 240

Ala Leu Ser Ser Thr Leu Gly Glu Ile Phe Leu Leu Gln Asn Ser Gln
                245                 250                 255

Ala Met Pro Asp Val Ala Trp Asn Arg Leu Ser Gly Glu Glu Asn Trp
            260                 265                 270

Ile Ser Leu Leu Ser Leu His Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Glu Gln Leu Arg Asn Ala Asp Lys Leu Asp Leu Lys Asn
385                 390                 395                 400

Asn Pro Ala Arg Ile Val Pro Ile Ala Ile Glu Gly Cys Glu Asn Glu
                405                 410                 415

Gly Asp Asn Lys Leu Cys Gln Leu Glu Thr Phe Gln Lys Lys Val Ala
            420                 425                 430
```

Gln Val Ile Glu Pro Ala Cys His Ile
    435                 440

<210> SEQ ID NO 12
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 12

| | |
|---|---|
| atgacaatag caaaagaata tctgcggtta tccatactca ctttggtgct cagtagtttt | 60 |
| acgctaagtg ctgcaccgct tgcagcacaa tctaccggtt acactttgga gcgcgtggtg | 120 |
| attttgagcc gccacggtgt tcgttccccg acgaaacaaa cacagttaat gaatgatgtt | 180 |
| acaccggaca atggccaca atggccagta aaagcgggct atttaacgcc gcgaggggca | 240 |
| ggattagtca ctttaatggg cgggttctat ggtgattatt ccgcagcta tgggttgtta | 300 |
| ccggcgggt gcccggcaga cgaatccatc tatgtgcaag ctgatgttga ccaacgtacc | 360 |
| cgcttaaccg ggcaggcatt tctggacggt atagccccgg attgcggcct gaaagtacat | 420 |
| tatcaagctg atttgaaaaa aattgaccca ttgttccata ccgtcgaggc ggggggtatgt | 480 |
| aaaggcgacc cagagaaaac tcatcaggct gttgaaaaac gcttgggtgg gccattaaat | 540 |
| gaactgagtc aacgctatgc caagcccttt gccctgatgg gcgaggtgct gaattttcg | 600 |
| gcctcacctt attgcaactc actgcaacag aaaggaaaaa cctgtgattt tgcgactttt | 660 |
| gcagcaaatg aaatcgaggt aaataaagaa gggacaaaag tctcactgag tgggccattg | 720 |
| gcgctatcat cgacattagg tgaaattttc ctattacaaa attcacaggc catgccagat | 780 |
| gtcgcctgga accgtctcag cggtgaagaa aattggattt cattattgtc actgcataat | 840 |
| gcacagttcg atttgatggc caaaaccct tatatcgccc ggcataaagg aactccgttg | 900 |
| ttgcaacaaa ttgatacggc attagtgttg caacgtgatg ctcagggca aacactgccg | 960 |
| ctgtcaccgc aaaccaaatt gctgttcctc gggggacatg acaccaatat tgccaatatt | 1020 |
| gcgggtatgt tagggccaa ttggcaatta ccgcagcaac ctgataatac cccgccaggc | 1080 |
| ggagggctag tctttgagct atggcagaat ccggataacc atcaacgcta tgtggcggtg | 1140 |
| aaaatgttct atcaaacgat ggagcagttg cgcaatgcag ataagttaga tttgaaaaac | 1200 |
| aacccggcaa gaattgttcc cattgctatt gaagggtgtg aaaacgaggg tgataacaaa | 1260 |
| ctttgtcagc ttgaaacgtt ccaaaagaaa gtcgcccaag tgatcgagcc agcctgccat | 1320 |
| atttaa | 1326 |

<210> SEQ ID NO 13
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 13

| | |
|---|---|
| atgacaatag caaaagaata tctgcggtta tccatactca ctttggtgct cagtagtttt | 60 |
| acgctaagtg ctgcaccgct tgcagcacaa tctaccggtt acactttgga gcgcgtggtg | 120 |
| attttgagcc gccacggtgt tcgttccccg acgaaacaaa cacagttaat gaatgatgtt | 180 |
| acaccggaca atggccaca atggccagta aaagcgggct atttaacgcc gcgaggggca | 240 |
| ggattagtca ctttaatggg cgggttctat ggtgattatt ccgcagcta tgggttgtta | 300 |

```
ccggcggggt gcccggcaga cgaatccatc tatgtgcaag ctgatgttga ccaacgtacc    360
cgcttaaccg ggcaggcatt tctggacggt atagccccgg attgcggcct gaaagtacat    420
tatcaagctg atttgaaaaa aattgaccca ttgttccata ccgtcgaggc gggggtatgt    480
aaagcggacc cagagaaaac tcatcaggct gttgaaaaac gcttgggtgg gccattaaat    540
gaactgagtc aacgctatgc caagcccttt gccctgatgg gcgaggtgct gaattttcg     600 gcctcacctt attgcaactc actgcaacag aaaggaaaaa cctgtgattt tgcgactttt    660
gcagcaaatg aaatcgaggt aaataaagaa gggacaaaag tctcactgag tgggccattg    720
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaacccct tatatcgccc ggcataaagg aactccgttg    900
ttgcaacaaa ttgatacggc attagtgttg caacgtgatg ctcaggggca aacactgccg    960
ctgtcaccgc aaaccaaatt gctgttcctc gggggacatg acaccaatat tgccaatatt   1020
gcgggtatgt taggggccaa ttggcaatta ccgcagcaac tgataatac cccgccaggc    1080 ggagggctag tctttgagct atggcagaat ccggataacc atcaacgcta tgtggcggtg   1140
aaaatgttct atcaaacgat ggagcagttg cgcaatgcag ataagttaga tttgaaaaac   1200
aacccggcaa gaattgttcc cattgctatt gaagggtgtg aaaacgaggg tgataacaaa   1260 cttttgtcagc ttgaaacgtt ccaaaagaaa gtcgcccaag tgatcgagcc agcctgccat   1320
atttaa                                                              1326

<210> SEQ ID NO 14
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 14
atgacaatag caaaagaata tctgcggtta tccatactca ctttggtgct cagtagtttt     60
acgctaagtg ctgcaccgct tgcagcacaa tctaccggtt acactttgga gcgcgtggtg    120
attttgagcc gccacggtgt tcgttccccg acgaaacaaa cacagttaat gaatgatgtt    180
acaccggaca atggccaca atggccagta aaagcgggct atttaacgcc gcgaggggca    240
ggattagtca ctttaatggg cgggttctat ggtgattatt ccgcagcta tgggttgtta    300 ccggcggggt gcccggcaga cgaatccatc tatgtgcaag ctgatgttga ccaacgtacc    360
cgcttaaccg ggcaggcatt tctggacggt atagccccgg attgcggcct gaaagtacat    420
tatcaagctg atttgaaaaa aattgaccca ttgttccata ccgtcgaggc gggggtatgt    480
aaagcggacc cagagaaaac tcatcaggct gttgaaaaac gcttgggtgg gccattaaat    540
gaactgagtc aacgctatgc caagcccttt gccctgatgg gcgaggtgct gaattttcg     600 gcctcacctt attgcaactc actgcaacag aaaggaaaaa cctgtgattt tgcgactttt    660
gcagcaaatg aaatcgaggt aaataaaggc gggacaaaag tctcactgag tgggccattg    720
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaacccct tatatcgccc ggcataaagg aactccgttg    900
ttgcaacaaa ttgatacggc attagtgttg caacgtgatg ctcaggggca aacactgccg    960
ctgtcaccgc aaaccaaatt gctgttcctc gggggacatg acaccaatat tgccaatatt   1020
```

```
gcgggtatgt tagggGccaa ttggcaatta ccgcagcaac ctgataatac cccgccaggc   1080
ggagggctag tctttgagct atggcagaat ccggataacc atcaacgcta tgtggcggtg   1140
aaaatgttct atcaaacgat ggagcagttg cgcaatgcag ataagttaga tttgaaaaac   1200
aacccggcaa gaattgttcc cattgctatt gaagggtgtg aaaacgaggg tgataacaaa   1260
ctttgtcagc ttgaaacgtt ccaaaagaaa gtcgcccaag tgatcgagcc agcctgccat   1320
atttaa                                                              1326
```

<210> SEQ ID NO 15
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 15

```
atgacaatag caaaagaata tctgcggtta tccatactca ctttggtgct cagtagtttt     60
acgctaagtg ctgcaccgct tgcagcacaa tctaccggtt acactttgga gcgcgtggtg    120
attttgagcc gccacggtgt tcgttccccg acgaaacaaa cacagttaat gaatgatgtt    180
acaccggaca atggccaca atggccagta aaagcgggct atttaacgcc gcgagggca     240 ggattagtca ctttaatggg cgggttctat ggtgattatt ccgcagcta tgggttgtta     300 ccggcgggt gcccggcaga cgaatccatc tatgtgcaag ctgatgttga ccaacgtacc    360
cgcttaaccg gcaggcatt tctggacggt atagccccgg attgcggcct gaaagtacat    420
tatcaagctg atttgaaaaa aattgaccca ttgttccata ccgtcgaggc ggggtatgt    480 aaagcggacc cagagaaaac tcatcaggct gttgaaaaac gcttgggtgg gccattaaat    540
gaactgagtc aacgctatgc caagcccttt gccctgatgg gcgaggtgct gaattttcg     600 gcctcacctt attgcaactc actgcaacag aaaggaaaaa cctgtgattt tgcgactttt     660
gcagcaaatg aaatcgaggt aaataaagcg gggacaaaag tctcactgag tgggccattg    720
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaaccct tatatcgccc ggcataaagg aactccgttg    900
ttgcaacaaa ttgatacggc attagtgttg caacgtgatg ctcaggggca acactgccg     960 ctgtcaccgc aaaccaaatt gctgttcctc gggggacatg acaccatat tgccaatatt   1020 gcgggtatgt taggggccaa ttggcaatta ccgcagcaac ctgataatac cccgccaggc   1080
ggagggctag tctttgagct atggcagaat ccggataacc atcaacgcta tgtggcggtg   1140
aaaatgttct atcaaacgat ggagcagttg cgcaatgcag ataagttaga tttgaaaaac   1200
aacccggcaa gaattgttcc cattgctatt gaagggtgtg aaaacgaggg tgataacaaa   1260
ctttgtcagc ttgaaacgtt ccaaaagaaa gtcgcccaag tgatcgagcc agcctgccat   1320
atttaa                                                              1326
```

<210> SEQ ID NO 16
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 16

```
atgacaatag caaaagaata tctgcggtta ccatactca ctttggtgct cagtagtttt    60
acgctaagtg ctgcaccgct tgcagcacaa tctaccggtt acactttgga gcgcgtggtg   120
attttgagcc gccacggtgt tcgttccccg acgaaacaaa cacagttaat gaatgatgtt   180
acaccggaca aatggccaca atggccagta aaagcgggct atttaacgcc gcagggggca   240
ggattagtca ctttaatggg cgggttctat ggtgattatt ccgcagcta tgggttgtta    300 ccggcgggt gcccggcaga cgaatccatc tatgtgcaag ctgatgttga ccaacgtacc    360
cgcttaaccg ggcaggcatt tctggacggt atagccccgg attgcggcct gaaagtacat   420
tatcaagctg atttgaaaaa aattgaccca ttgttccata ccgtcgaggc gggggtatgt   480
aaagcggacc cagagaaaac tcatcaggct gttgaaaaac gcttgggtgg gccattaaat   540
gaactgagtc aacgctatgc caagcccttt gccctgatgg gcgaggtgct gaattttcg    600 gcctcacctt attgcaactc actgcaacag aaaggaaaaa cctgtgattt tgcgactttt   660
gcagcaaatg aaatcgaggt aaataaatct gggacaaaag tctcactgag tgggccattg   720
gcgctatcat cgacattagg tgaaattttc ctattacaaa attcacaggc catgccagat   780
gtcgcctgga accgtctcag cggtgaagaa aattggattt cattattgtc actgcataat   840
gcacagttcg atttgatggc caaaaccct tatatcgccc ggcataaagg aactccgttg    900
ttgcaacaaa ttgatacggc attagtgttg caacgtgatg ctcaggggca aacactgccg   960
ctgtcaccgc aaaccaaatt gctgttcctc ggggacatg acaccaatat tgccaatatt   1020
gcgggtatgt tagggccaa ttggcaatta ccgcagcaac ctgataatac cccgccaggc   1080
ggagggctag tctttgagct atggcagaat ccggataacc atcaacgcta tgtggcggtg   1140 aaatgttct atcaaacgat ggagcagttg cgcaatgcag ataagttaga tttgaaaaac   1200
aacccggcaa gaattgttcc cattgctatt gaagggtgtg aaaacgaggg tgataacaaa   1260
ctttgtcagc ttgaaacgtt ccaaaagaaa gtcgcccaag tgatcgagcc agcctgccat   1320
atttaa                                                            1326
```

<210> SEQ ID NO 17  
<211> LENGTH: 1326  
<212> TYPE: DNA  
<213> ORGANISM: Artificial Sequence  
<220> FEATURE:  
<223> OTHER INFORMATION: VARIANT Gene

<400> SEQUENCE: 17

```
atgacaatag caaaagaata tctgcggtta ccatactca ctttggtgct cagtagtttt    60
acgctaagtg ctgcaccgct tgcagcacaa tctaccggtt acactttgga gcgcgtggtg   120
attttgagcc gccacggtgt tcgttccccg acgaaacaaa cacagttaat gaatgatgtt   180
acaccggaca aatggccaca atggccagta aaagcgggct atttaacgcc gcagggggca   240
ggattagtca ctttaatggg cgggttctat ggtgattatt ccgcagcta tgggttgtta    300 ccggcgggt gcccggcaga cgaatccatc tatgtgcaag ctgatgttga ccaacgtacc    360
cgcttaaccg ggcaggcatt tctggacggt atagccccgg attgcggcct gaaagtacat   420
tatcaagctg atttgaaaaa aattgaccca ttgttccata ccgtcgaggc gggggtatgt   480
aaagcggacc cagagaaaac tcatcaggct gttgaaaaac gcttgggtgg gccattaaat   540
gaactgagtc aacgctatgc caagcccttt gccctgatgg gcgaggtgct gaattttcg    600 gcctcacctt attgcaactc actgcaacag aaaggaaaaa cctgtgattt tgcgactttt   660
gcagcaaatg aaatcgaggt aaataaaacc gggacaaaag tctcactgag tgggccattg   720
```

```
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaacccct tatatcgccc ggcataaagg aactccgttg    900
ttgcaacaaa ttgatacggc attagtgttg caacgtgatg ctcaggggca aacactgccg    960
ctgtcaccgc aaaccaaatt gctgttcctc ggggacatg acaccaatat tgccaatatt    1020
gcgggtatgt taggggccaa ttggcaatta ccgcagcaac ctgataatac cccgccaggc    1080
ggagggctag tctttgagct atggcagaat ccggataacc atcaacgcta tgtggcggtg    1140
aaaatgttct atcaaacgat ggagcagttg cgcaatgcag ataagttaga tttgaaaaac    1200
aacccggcaa gaattgttcc cattgctatt gaagggtgtg aaaacgaggg tgataacaaa    1260
ctttgtcagc ttgaaacgtt ccaaaagaaa gtcgcccaag tgatcgagcc agcctgccat    1320
atttaa                                                               1326

<210> SEQ ID NO 18
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 18
atgacaatag caaaagaata tctgcggtta tccatactca ctttggtgct cagtagtttt    60
acgctaagtg ctgcaccgct tgcagcacaa tctaccggtt acacttggga gcgcgtggtg    120
attttgagcc gccacggtgt tcgttccccg acgaaacaaa cacagttaat gaatgatgtt    180
acaccggaca atggccaca atggccagta aaagcgggct atttaacgcc gcgaggggca    240
ggattagtca ctttaatggg cgggttctat ggtgattatt ccgcagcta tgggttgtta    300 ccggcggggt gccgggcaga cgaatccatc tatgtgcaag ctgatgttga ccaacgtacc    360
cgcttaaccg ggcaggcatt tctggacggt atagccccgg attgcggcct gaaagtacat    420
tatcaagctg atttgaaaaa aattgaccca ttgttccata ccgtcgaggc gggggtatgt    480
aaagcggacc cagagaaaac tcatcaggct gttgaaaaac gcttgggtgg gccattaaat    540
gaactgagtc aacgctatgc caagcccttt gccctgatgg gcgaggtgct gaattttcg    600 gcctcacctt attgcaactc actgcaacag aaaggaaaaa cctgtgattt tgcgactttt    660
gcagcaaatg aaatcgaggt aaataaagat gggacaaaag tctcactgag tgggccattg    720
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaacccct tatatcgccc ggcataaagg aactccgttg    900
ttgcaacaaa ttgatacggc attagtgttg caacgtgatg ctcaggggca aacactgccg    960
ctgtcaccgc aaaccaaatt gctgttcctc ggggacatg acaccaatat tgccaatatt    1020
gcgggtatgt taggggccaa ttggcaatta ccgcagcaac ctgataatac cccgccaggc    1080
ggagggctag tctttgagct atggcagaat ccggataacc atcaacgcta tgtggcggtg    1140
aaaatgttct atcaaacgat ggagcagttg cgcaatgcag ataagttaga tttgaaaaac    1200
aacccggcaa gaattgttcc cattgctatt gaagggtgtg aaaacgaggg tgataacaaa    1260
ctttgtcagc ttgaaacgtt ccaaaagaaa gtcgcccaag tgatcgagcc agcctgccat    1320
atttaa                                                               1326
```

<210> SEQ ID NO 19
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 19

```
atgacaatag caaaagaata tctgcggtta tccatactca ctttggtgct cagtagtttt      60
acgctaagtg ctgcaccgct tgcagcacaa tctaccggtt acactttgga gcgcgtggtg     120
attttgagcc gccacggtgt tcgttccccg acgaaacaaa cacagttaat gaatgatgtt     180
acaccggaca aatggccaca atggccagta aaagcgggct atttaacgcc gcgaggggca     240
ggattagtca ctttaatggg cgggttctat ggtgattatt ccgcagcta tgggttgtta      300
ccggcggggt gcccggcaga cgaatccatc tatgtgcaag ctgatgttga ccaacgtacc     360
cgcttaaccg ggcaggcatt tctggacggt atagccccgg attgcggcct gaaagtacat     420
tatcaagctg atttgaaaaa aattgaccca ttgttccata ccgtcgaggc ggggggtatgt    480
aaagcggacc cagagaaaac tcatcaggct gttgaaaaac gcttgggtgg gccattaaat    540
gaactgagtc aacgctatgc caagccctt gccctgatgg gcgaggtgct gaattttcg      600
gcctcacctt attgcaactc actgcaacag aaaggaaaaa cctgtgattt tgcgactttt     660
gcagcaaatg aaatcgaggt aaataaaccg gggacaaaag tctcactgag tgggccattg    720
gcgctatcat cgacattagg tgaaattttc ctattacaaa attcacaggc catgccagat     780
gtcgcctgga accgtctcag cggtgaagaa aattggattt cattattgtc actgcataat     840
gcacagttcg atttgatggc caaaacccct tatatcgccc ggcataaagg aactccgttg    900
ttgcaacaaa ttgatacggc attagtgttg caacgtgatg ctcaggggca aacactgccg     960
ctgtcaccgc aaaccaaatt gctgttcctc gggggacatg acaccaatat tgccaatatt    1020
gcgggtatgt taggggccaa ttggcaatta ccgcagcaac ctgataatac cccgccaggc    1080
ggagggctag tctttgagct atggcagaat ccggataacc atcaacgcta tgtggcggtg    1140
aaaatgttct atcaaacgat ggagcagttg cgcaatgcag ataagttaga tttgaaaaac    1200
aacccggcaa gaattgttcc cattgctatt gaagggtgtg aaaacgaggg tgataacaaa    1260
ctttgtcagc ttgaaacgtt ccaaaagaaa gtcgcccaag tgatcgagcc agcctgccat    1320
atttaa                                                             1326
```

<210> SEQ ID NO 20
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 20

```
atgacaatag caaaagaata tctgcggtta tccatactca ctttggtgct cagtagtttt      60
acgctaagtg ctgcaccgct tgcagcacaa tctaccggtt acactttgga gcgcgtggtg     120
attttgagcc gccacggtgt tcgttccccg acgaaacaaa cacagttaat gaatgatgtt     180
acaccggaca aatggccaca atggccagta aaagcgggct atttaacgcc gcgaggggca     240
ggattagtca ctttaatggg cgggttctat ggtgattatt ccgcagcta tgggttgtta      300
ccggcggggt gcccggcaga cgaatccatc tatgtgcaag ctgatgttga ccaacgtacc     360
cgcttaaccg ggcaggcatt tctggacggt atagccccgg attgcggcct gaaagtacat     420
```

```
tatcaagctg atttgaaaaa aattgaccca ttgttccata ccgtcgaggc gggggtatgt    480
aaagcggacc cagagaaaac tcatcaggct gttgaaaaac gcttgggtgg gccattaaat    540
gaactgagtc aacgctatgc caagcccttt gccctgatgg gcgaggtgct gaattttcg     600 gcctcacctt attgcaactc actgcaacag aaaggaaaaa cctgtgattt tgcgactttt    660
gcagcaaatg aaatcgaggt aaataaacgt gggacaaaag tctcactgag tgggccattg    720
gcgctatcat cgacattagg tgaaattttc ctattacaaa attcacaggc catgccagat    780
gtcgcctgga accgtctcag cggtgaagaa aattggattt cattattgtc actgcataat    840
gcacagttcg atttgatggc caaaacccct tatatcgccc ggcataaagg aactccgttg    900
ttgcaacaaa ttgatacggc attagtgttg caacgtgatg ctcagggca  aacactgccg    960 ctgtcaccgc aaaccaaatt gctgttcctc ggggacatg  acaccaatat tgccaatatt   1020
gcgggtatgt tagggccaa  ttggcaatta ccgcagcaac ctgataatac cccgccaggc   1080
ggagggctag tctttgagct atggcagaat ccggataacc atcaacgcta tgtggcggtg   1140
aaaatgttct atcaaacgat ggagcagttg cgcaatgcag ataagttaga tttgaaaaac   1200
aacccggcaa gaattgttcc cattgctatt gaagggtgtg aaaacgaggg tgataacaaa   1260
ctttgtcagc ttgaaacgtt ccaaaagaaa gtcgcccaag tgatcgagcc agcctgccat   1320
atttaa                                                              1326
```